US00PP25824P3

(12) United States Plant Patent
Carbajal

(10) Patent No.: US PP25,824 P3
(45) Date of Patent: Aug. 18, 2015

(54) *ZOYSIA JAPONICA* PLANT NAMED 'DR2011'

(50) Latin Name: *Zoysia japonica*
Varietal Denomination: DR2011

(71) Applicant: Francisco Carbajal, New Smyrna, FL (US)

(72) Inventor: Francisco Carbajal, New Smyrna, FL (US)

( * ) Notice: Subject to any disclaimer, the term of this patent is extended or adjusted under 35 U.S.C. 154(b) by 81 days.

(21) Appl. No.: 13/998,926

(22) Filed: Dec. 23, 2013

(65) Prior Publication Data

US 2015/0181795 P1 Jun. 25, 2015

(51) Int. Cl.
*A01H 5/00* (2006.01)

(52) U.S. Cl.
USPC ..... Plt./390

(58) Field of Classification Search
USPC ..... Plt./390
See application file for complete search history.

*Primary Examiner* — Annette Para
(74) *Attorney, Agent, or Firm* — Samual R. McCoy, Jr.

(57) ABSTRACT

A new and distinct cultivar of *Zoysia japonica* plant named 'DR2011', characterized by the combination of a medium leaf blade, bright green foliage color, and a natural resistance to scalping; characteristics which are of commercial value.

1 Drawing Sheet

Latin name of genus and species of plant claimed: The Latin name of the genus and species of the novel variety disclosed herein is *Zoysia japonica.*

Variety denomination: The novel variety of *Zoysia japonica* disclosed herein has been given the variety denomination 'DR2011'.

BACKGROUND OF THE INVENTION

The present invention relates to a new and distinct perennial variety of *Zoysia japonica,* which has been given the variety denomination of 'DR2011'. Its market class is that of a turf grass. 'DR2011' is intended for use as a lawn grass in gardening, landscaping, sports fields and amenity horticulture.

PARENTAGE

The new *Zoysia japonica* cultivar was discovered as a spontaneous mutation in a controlled, irrigated and full-sun planting of *Zoysia japonica* (unpatented and unnamed) at a commercial turf grass production operation in New Smyrna Beach, Fla., USA. The spontaneous mutation was observed to possess a medium leaf blade and to retain a bright green turf color and exceptional turf quality, in a soil known to have poor fertility; essentially giving the appearance of a healthy turf under a low-fertility maintenance regimen. Additionally, the instant mutation did not appear to suffer an affect known as "scalping" when mowed infrequently. Scalping occurs when a turf grass is mowed below the intended point of contact (i.e. the leaf blade) and severed at the culm, thereby removing the entire leaf canopy and creating a generally brown or straw-like appearance of the turf stand and weakening the turf.

Stolons of said spontaneous mutation were collected in July of 2011 for further evaluation and the confirmation of the distinctive characteristics observed in the field. Said stolons were planted into multiple plant propagation trays (also known as "plug trays"), and were grown using typical nursery production procedure at the Inventor's commercial turf grass farm in New Smyrna Beach, Fla. The resultant rooted "plugs" were transplanted to an in-ground field plot for further observation. After approximately one year, the distinguishing characteristics initially observed were confirmed and the new cultivar was given the designation of 'DR2011'.

ASEXUAL REPRODUCTION

'DR2011' was first asexually propagated by cutting and division of stolons and rhizomes in July of 2011 in New Smyma Beach, Fla. 'DR2011' has since been further asexually propagated by means of cutting and division of stolons and rhizomes through two generations. The distinctive characteristics of the variety have remained stable and true to type through successive cycles of asexual propagation.

SUMMARY OF THE INVENTION

A new and distinct cultivar of *Zoysia japonica* plant named 'DR2011', characterized by the combination of a medium leaf blade, bright green foliage color, and a natural resistance to scalping; characteristics which are of commercial value.

BRIEF DESCRIPTION OF THE PHOTOGRAPHS

The FIGURE illustrates a 14 month-old planting of 'DR2011', as nearly true as it is reasonably possible to make the same in color illustrations of this type. Colors in the photographs differ slightly from the color values cited in the detailed description, which accurately describes the colors of 'DR2011'.

DETAILED BOTANICAL DESCRIPTION

The following is a detailed botanical description of a new and distinct variety of a *Zoysia japonica* turf grass plant known as 'DR2011'. Plant observations were made on propagules harvested from a 14 month-old planting at a commercial turf grass production operation in New Smyrna Beach, Fla., USA. Unless indicated otherwise, the descriptions disclosed herein are based upon observations made in November 2013 of mature 'DR2011' grown in full sun and in accordance with commonly accepted turfgrass production practices, with two applications of slow-release fertilize and overhead irrigation as needed. No pest and disease measures were taken. Mowing regimen would be classified as infrequent; that is, less than twice a month.

Those skilled in the art will appreciate that certain characteristics will vary with older or, conversely, younger plants. 'DR2011' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on *The Royal Horticultural Society Color Chart*, of The Royal Horticultural Society, London, 1986 edition.

TECHNICAL DESCRIPTION OF THE VARIETY

Plant description:

*Propagation.*—Typical time to develop roots is similar to that of other *Zoysia* grasses; approximately 2 to 4 weeks. Average crop time to produce an initial mature and marketable stand of turf grass sod is approximately 7 to 9 months. Precise timing varies depending on fertilizer and water inputs as well as geographical location.

*Growth habit.*—Perennial plant with a prostrate growth habit forming a tight mat of stolons which root adventitiously on the ground surface and branch heavily at the stolon nodes. Culms are prostrate, becoming decumbent when flowering. Root system is typical for that of *Zoysia* grass species; a network of rhizomes and fibrous feeder roots.

*Growth rate.*—Moderate to vigorous.

*Stolon length.*—Longest observed stolon is 70 mm.

*Stolon width.*—Approximately 1 mm.

*Stolon color* (*adaxial & abaxial*).—Juvenile: Yellow-Green 145B; mature: Orange-White 159A.

*Stolon internode length.*—As measured, 10 to 16 mm on mature stolons.

Foliage:

*Attachment.*—Cauline.

*Culm attitude.*—Prostrate to semi-decumbent when flowering.

*Culm length.*—Most mature culm observed measures at 73 mm, from stolon node to apex.

*Culm internode length.*—Ranging from 10 to 16 mm.

*Length of blade.*—Mature blades are an average of 75 mm.

*Width of blade.*—Widest, measuring 4 mm.

*Shape of blade.*—Linear.

*Leaf shape; apex.*—Acute.

*Leaf aspect.*—Concave.

*Margin.*—Entire.

*Texture* (*adaxial & abaxial surfaces*).—Smooth.

*Hairiness* (*adaxial & abaxial surfaces*).—Glabrous.

*Leaf color* (*adaxial surface*).—Juvenile: 137B; mature: 137B.

*Leaf color* (*abaxial surface*).—Juvenile: 137C; mature: 137C.

*Venation: type.*—Parallel.

*Venation color.*—Indistinguishable.

*Leaf sheath.*—Glabrous, ranging from 8 to 10 mm long. Color approximates to Yellow-Green 145A

*Collar.*—Approximately 1 mm, and constricted. Color approximates to Yellow-Green 146C.

*Ligule.*—A fringe of approximately 10 to 15 hairs, ranging in length from 1 to 3 mm.

Flower:

*Natural flowering season.*—Spring to fall; in Northern hemisphere, April to November.

*Inflorescence type and habit.*—Spike-like raceme.

*Total inflorescence size.*—25 mm long by 1 mm wide.

*Rachilla.*—Curved; approximately 2 mm in length; width is minute; color is closest to Green 145B.

*Quantity of spikelets per raceme.*—14 to 18 florets.

*Color of spikelets.*—The immature lemmas are Yellow-Green (RHS 146A) and mature to a Grayed-Purple corresponding to 183B.

*Shape of spikelets.*—Narrowly ovoid with an acute apex.

*Dimensions of spikelets.*—Approximately 2 mm long and less than 1 mm wide.

*Glumes.*—Absent.

*Awns.*—Absent.

Reproductive organs:

*Stamens.*—Not observed.

*Style.*—Not observed in most *Zoysia* sp., including 'DR2011'.

*Stigma.*—Featherlike; length is approximately 1 mm; wide is minute; color is Yellow-Green 154D.

*Ovary.*—Not observed.

Seeds and fruits: The number of seed per raceme, seed dimensions and color of seed correspond to the number of spikelets, spikelet dimensions and spike color.

Environmental tolerances:

*Disease/pest resistance.*—Neither tolerance nor resistance to normal diseases and pests of *Zoysia japonica* has been observed.

*Temperature tolerance.*—*Zoysia japonica* is known to tolerate temperatures from approximately 10 degrees F. to at 115 degrees F.

*Drought tolerance.*—Like other *Zoysia species,* 'DR2011' exhibits good drought tolerance relative to other Genus of warm season grasses such as *Stenotaphrum* sp.

*Soil tolerances.*—Tolerant of most soil types; from sandy loam to loamy clay; maintains good turf quality in low-fertility soils.

COMPARISON OF 'DR2011' WITH OTHER VARIETIES OF *ZOYSIA JAPONICA*

The closest known comparator to 'DR2011' is *Zoysia japonica* 'Zenith' (not patented). While similar in foliage color, texture and environmental tolerances, there are certain differences which distinguish 'DR2011' from 'Zenith'. 'DR2011' produces fewer inflorescences, produces a dense foliage canopy, and the foliage attitude is more prostrate.

While both the claimed plant and the comparator are noted for deep green foliage color, 'DR2011' exhibits a darker green foliage color when compared to 'Zenith'. The adaxial leaf surface of 'DR2011' is green 1378, whereas the adaxial leaf surface of 'Zenith' approximates to 138A.

'DR2011' has a more prostrate culm attitude compared to that of 'Zenith' which has a decumbent culm attitude. The prostrate nature of 'DR2011' makes it less prone to scalping compared to 'Zenith'. It is believed that the prostrate nature of the culms also attributes to the greater turf density when compared to the turf density of 'Zenith'.

It is estimated that 'Zenith' will produce twice as many inflorescence as 'DR2011'.

Differences in foliage dimensions distinguish the claimed plant from 'Zenith'. 'DR2011'; has a foliage length of 75 mm and a width of 4.0 mm whereas 'Zenith' has a length of 80 mm and a width of 3.0 mm, which gives 'DR2011' a broader leaf texture.

That which is claimed is:

1. A new and distinct variety of *Zoysia japonica* plant named 'DR2011', substantially as described and illustrated herein.

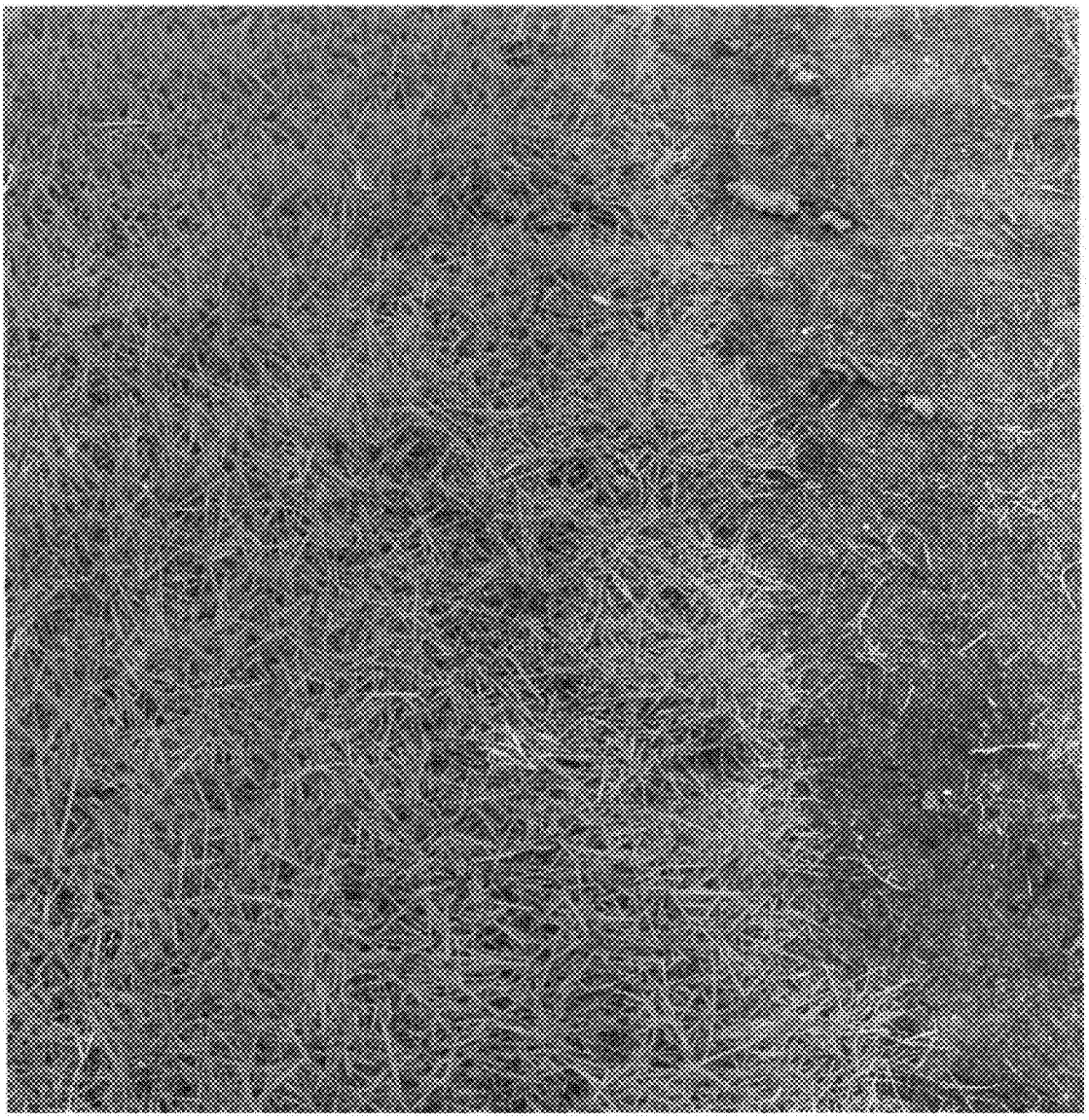

* * * * *